(12) United States Patent
Farmer et al.

(10) Patent No.: US 10,323,225 B2
(45) Date of Patent: Jun. 18, 2019

(54) APPARATUS, SYSTEMS AND METHODS FOR GROWING MICROORGANISMS

(71) Applicant: Locus Solutions, LLC, Solon, OH (US)

(72) Inventors: Sean Farmer, Miami, FL (US); Sharmistha Mazumder, Copley, OH (US); Xiao-Zhou Zhang, Solon, OH (US); Maja Milovanovic, North Royalton, OH (US)

(73) Assignee: Locus Solutions, Solon, OH (US)

( * ) Notice: Subject to any disclaimer, the term of this patent is extended or adjusted under 35 U.S.C. 154(b) by 0 days.

(21) Appl. No.: 15/298,348

(22) Filed: Oct. 20, 2016

(65) Prior Publication Data
US 2017/0107477 A1 Apr. 20, 2017

Related U.S. Application Data (60) Provisional application No. 62/243,733, filed on Oct. 20, 2015.

(51) Int. Cl.
| | |
|---|---|
| *C12M 1/36* | (2006.01) |
| *C12N 1/20* | (2006.01) |
| *C12M 3/00* | (2006.01) |
| *C12M 1/00* | (2006.01) |

(52) U.S. Cl.
CPC .......... *C12M 41/48* (2013.01); *C12M 23/42* (2013.01); *C12M 23/52* (2013.01); *C12N 1/20* (2013.01)

(58) Field of Classification Search
None
See application file for complete search history.

(56) References Cited

U.S. PATENT DOCUMENTS

| | | |
|---|---|---|
| 4,426,450 A | 1/1984 | Donofrio |
| 5,447,866 A | 9/1995 | Runyon |
| 5,807,485 A | 9/1998 | Caplan et al. |
| 5,833,857 A | 11/1998 | Roth |
| 6,207,056 B1 | 3/2001 | Lucido et al. |
| 6,335,191 B1 | 1/2002 | Kiplinger et al. |
| 6,599,425 B2 | 7/2003 | Tartakovsky et al. |
| 7,044,152 B2 | 5/2006 | Scalzi et al. |
| 7,132,050 B2 | 11/2006 | Davis et al. |
| 7,485,224 B2 | 2/2009 | Jones et al. |
| 7,579,163 B2 | 8/2009 | Eriksen et al. |
| 7,615,156 B2 | 11/2009 | Lenger et al. |
| 7,674,380 B2 | 3/2010 | Lee |
| 7,879,593 B2 | 2/2011 | Whiteman |
| 7,932,078 B2 | 4/2011 | Posseme et al. |
| 8,257,961 B2 | 9/2012 | Brahmbhatt |
| 8,513,003 B2 | 8/2013 | Moreno et al. |
| 8,980,602 B2 | 3/2015 | Medoff |
| 2009/0011492 A1 | 1/2009 | Berzin |
| 2010/0035342 A1 | 2/2010 | Cheng et al. |
| 2010/0155314 A1 | 6/2010 | Lenger et al. |
| 2011/0135917 A1 | 6/2011 | Abt |
| 2011/0151507 A1 | 6/2011 | van Walsem |
| 2011/0212493 A1 | 9/2011 | Hirschel et al. |
| 2012/0021401 A1 | 1/2012 | Ulitzur et al. |
| 2012/0021492 A1 | 1/2012 | Fielding et al. |
| 2012/0132548 A1 | 5/2012 | Galliher |
| 2013/0115588 A1 | 5/2013 | Davis et al. |
| 2013/0245830 A1* | 9/2013 | West ............... C12M 41/48 700/266 |
| 2013/0337108 A1* | 12/2013 | Van Hee ............ C12N 1/04 426/11 |
| 2014/0377843 A1 | 12/2014 | Alyamani |
| 2015/0111252 A1 | 4/2015 | Hirschel et al. |
| 2015/0175950 A1 | 6/2015 | Hirschel et al. |

FOREIGN PATENT DOCUMENTS

| | | |
|---|---|---|
| EP | 2819040 A1 | 6/2013 |
| WO | 9320440 | 10/1993 |
| WO | 2007136821 A1 | 11/2007 |
| WO | 2008082726 A2 | 7/2008 |
| WO | 2008088371 A2 | 7/2008 |
| WO | 2013158312 A1 | 10/2013 |
| WO | 2014036187 A1 | 3/2014 |
| WO | 2015001321 A1 | 1/2015 |
| WO | 2015077663 A1 | 5/2015 |

OTHER PUBLICATIONS

International Search Report and Written Opinion for International Application No. PCT/US2016/057842 dated Jan. 30, 2017.
International Search Report and Written Opinion for International Application No. PCT/US2016/057637 dated Feb. 3, 2017.
Office Action for U.S. Appl. No. 14/617,819 dated Jun. 14, 2017.
Roe, S., et al.,"BIOST: Technology Developments for a Space Bioprocessing Facility," Proceedings 5th Eur. Symp. on 'Life Science Research in Space,' Arcachon, France, Sep. 26-Oct. 1, 1993 (ESA SP-336, Aug. 1994).
Office Action for U.S. Appl. No. 15/297,491 dated Jan. 11, 2019.
Response filed in European Patent Application No. 16794105.3 dated Mar. 18, 2019.

* cited by examiner

*Primary Examiner* — Michelle F. Paguio Frising
(74) *Attorney, Agent, or Firm* — Calfee, Halter & Griswold LLP (57) ABSTRACT

A fermentation system includes a fermentation tank, a plurality of sensors operable to measure a plurality of fermentation system parameters, a plurality of mechanisms operable to control the fermentation system parameters, and a controller in electronic communication with the sensors and with the mechanisms. The controller includes a memory, a receiver circuit, a transmitting circuit, and a control circuit. The memory stores a plurality of recipes each defining user operating instructions and parameter settings. The receiver circuit is configured to receive a batch identification code associated in the memory with one of the recipes. The transmitting circuit is configured to communicate the user operating instructions defined by the associated one of the recipes. The control circuit is configured to operate the mechanisms to adjust the fermentation system parameters in accordance with the parameter settings defined by the associated one of the recipes.

15 Claims, 6 Drawing Sheets

APPARATUS, SYSTEMS AND METHODS FOR GROWING MICROORGANISMS

CROSS-REFERENCE TO RELATED APPLICATION

The present application claims priority to and all benefit of U.S. Provisional Patent Application Ser. No. 62/243,733, filed on Oct. 20, 2015, for APPARATUS, SYSTEMS AND METHODS FOR GROWING BACTERIA, the entire disclosure of which is fully incorporated herein by reference.

BACKGROUND

The use of live bacteria and other microorganisms has been successfully incorporated into a wide variety of applications, including, for example, waste remediation, enhanced oil recovery, agricultural control agents, pesticides, and mining. In most such applications, a high density of live microorganisms is desirable to maximize effectiveness and to minimize the amount of material to be transported and/or deployed for treatment. Stabilization, preservation, storage and transportation of live bacteria to a use site can kill a high percentage of the bacteria, and may also introduce foreign, undesirable microorganisms into the final product, which may significantly limit the effectiveness of the microbiological product.

SUMMARY

The present application contemplates systems and methods for assisting user operation of a batch process bioreactor to optimize microbiological growth of a selected microorganism.

In an exemplary embodiment, a method of preparing a batch of microbiological material is contemplated. In the exemplary method, a fermentation kit is provided to a user, the fermentation kit including a starter culture. A fermentation system is provided, and includes a fermentation tank, a plurality of sensors operable to measure a plurality of fermentation system parameters, a plurality of mechanisms operable to control the plurality of fermentation system parameters, and a controller in electronic communication with the plurality of sensors and with the plurality of mechanisms. The controller includes a memory having stored therein a plurality of recipes each defining user operating instructions and parameter settings specific to fermentation of one of a plurality of microbiological cultures including the starter culture. A batch identification code is provided to a user, with the batch identification code being associated in the memory of the controller with the one of the plurality of recipes specific to the starter culture. The batch identification code is communicated to the controller. The operating instructions defined by the associated one of the plurality of recipes are communicated from the controller to the user, with the operating instructions including instructions for one or more manual user operations performed using the fermentation system. Using the controller, the plurality of mechanisms are operated to adjust the plurality of fermentation system parameters in accordance with the parameter settings defined by the associated one of the plurality of recipes.

In another exemplary embodiment, a fermentation system includes a fermentation tank, a plurality of sensors assembled with the fermentation tank and operable to measure a plurality of fermentation system parameters, a plurality of mechanisms assembled with the fermentation tank and operable to control the plurality of fermentation system parameters, and a controller in electronic communication with the plurality of sensors and with the plurality of mechanisms. The controller includes a memory, a receiver circuit, a transmitting circuit, and a control circuit. The memory stores a plurality of recipes each defining user operating instructions and parameter settings specific to fermentation of one of a plurality of microorganisms. The receiver circuit is configured to receive from a user a batch identification code associated in the memory with one of the plurality of recipes. The transmitting circuit is configured to communicate to a user the user operating instructions defined by the associated one of the plurality of recipes. The control circuit is configured to operate the plurality of mechanisms to adjust the plurality of fermentation system parameters in accordance with the parameter settings defined by the associated one of the plurality of recipes.

BRIEF DESCRIPTION OF THE DRAWINGS

These and other features and advantages of the present invention will become better understood with regard to the following description and accompanying drawings in which.

DETAILED DESCRIPTION

The Detailed Description merely describes exemplary embodiments of the invention and is not intended to limit the scope of the claims in any way. Indeed, the invention is broader than and unlimited by the exemplary embodiments, and the terms used in the claims have their full ordinary meaning.

To provide more effective and more concentrated microbiological products, bacteria may be generated on site for dispensing directly to the intended application, without exposing the material to the risk of losses associated with further handling of the material.

On site generation of live bacteria, as a solution to eliminating losses associated with stabilization, preservation, storage and transportation of microbiological products, may present its own challenges. Conventional fermentation equipment for growing and dispensing bacteria is very expensive, such that the cost of the equipment itself may far exceed the efficiency gains associated with the increased density of live bacteria in the microbiological product, particularly in applications where treatment with live bacteria is not continuous (and may, for example, be limited to one or two applications per year). Further, production of a desired strain of bacteria on site has required on-site personnel with the expertise necessary to provide suitable conditions for the culturing and cultivation of the targeted microbiological cells, including, for example, time sensitive control of cleaning/sterilization, temperature, nutrient supply, pH, oxygenation, foaming, agitation, and dispensation of a submerged microbiological material or slurry.

According to an exemplary aspect of the present application, a mobile or portable bioreactor may be provided for on-site production of a microbiological product including a suitable amount of a desired strain of bacteria. Because the microbiological product (e.g., slurry or fluid) is generated on-site, without resort to the bacteria killing stabilization, preservation, storage and transportation processes of conventional bacteria production, a much higher density of live bacteria may be generated, thereby requiring a much smaller volume of the microbiological slurry for use in the on-site application. This allows for a scaled-down bioreactor (e.g., smaller fermentation tank, smaller supplies of starter material, nutrients, pH control agents, de-foaming agents) that facilitates the mobility and portability of the system.

To provide the desired portability for a fermentation system for growing microorganisms, a movable (e.g., wheeled and provided with a trailer hitch) platform may be provided to support all necessary systems for microorganism production, process monitoring and control. This type of fermentation system can be moved as close as possible to a site of microbial product application, thereby maximizing the concentration of live microorganisms in a dispensed microbial product (e.g., a microorganism-containing fluid or slurry). This self-contained fermentation system will not require any additional expensive or complex downstream equipment and systems for decontamination and neutralization of waste products due to the fact that the freshly manufactured microbial products will be immediately used in full at the site of operation. The mobile platform-based fermentation system allows the system to be easily relocated and adapted for use in a different application and at a different location.

Figure 1:
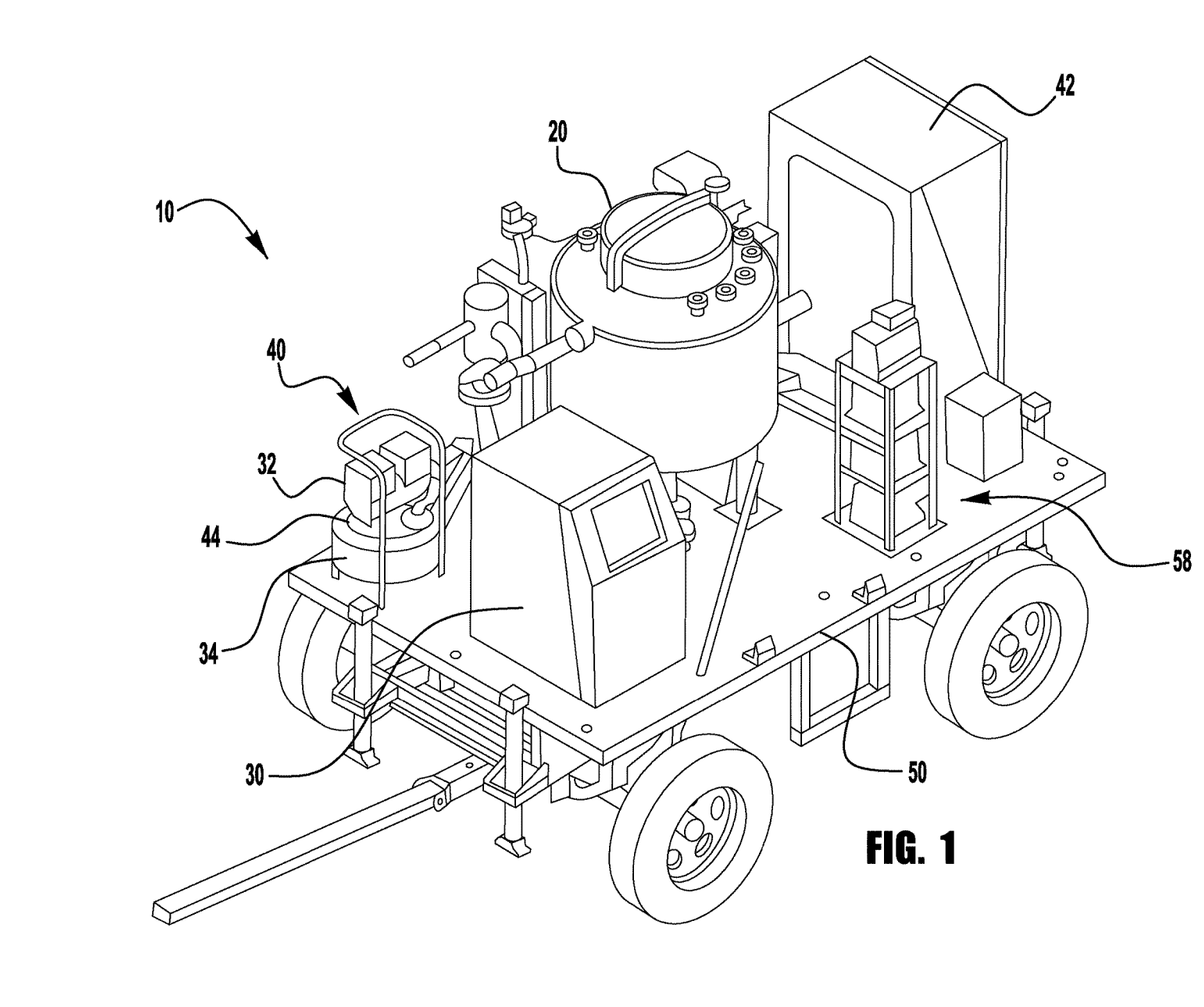
FIG. 1 depicts a partially exploded front perspective view of an of an apparatus for culturing and delivering microorganism products.
Figure 2:
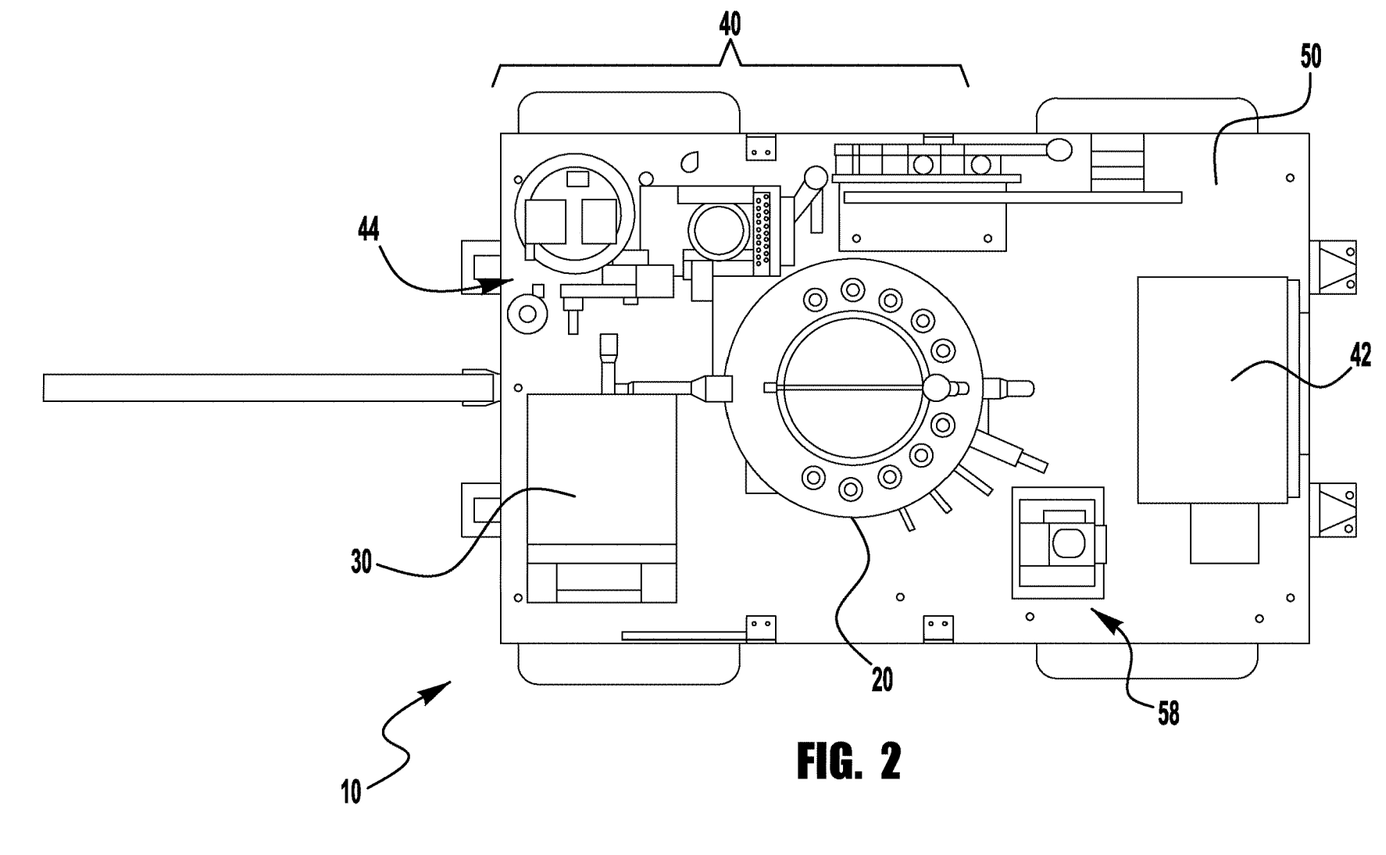
FIG. 2 is a top plan view thereof.

Referring now to FIG. 1-2, an apparatus for culturing and delivering biologically active products in a distributive, smaller scale and more timely and efficient manner is shown, generally noted as 10, according to an exemplary embodiment of the present invention. The apparatus 10 includes, generally, a bioreactor 20, a controller 30, a supply manifold 40, and a portable frame or support structure 50.

The bioreactor 20 is adapted for the culturing of microbiological animal or plant cells. While the exemplary embodiments disclosed herein are directed to a submerged batch cultivation method or its equivalents, many of the inventive features described herein may relate to other methods of bacterial growth, including, for example, continuous submerged cultivation (e.g., a chemostat), and growth or collection of bacteria on a substrate surface.

The bioreactor 20 in any configuration should provide suitable conditions for the culturing and cultivation of the targeted microbiological, animal or plant cells, and may include aseptic precautions, nutrients, optimum temperature and pH, oxygenation and agitation, for the growth of microorganisms. The reaction vessel 20 may be built out of metal such as copper or steel and incorporate a water cooling jacket for control of temperature during a reaction. Once the reaction process produces heat, the flow of cooling fluid can keep the internal media temperature at optimum temperature. The bioreactor 20 may further include provisions for cleaning and sterilizing, either through the injection of steam, hot water, or aseptic cleaning fluids between production cycles.

The bioreactor 20 includes one or more mechanisms for oxygenation of the culture liquid to supply oxygen needed for bacterial growth. Exemplary mechanisms include impellers for mechanical agitation of the liquid, and air spargers for supplying bubbles of gas to the liquid for dissolution of oxygen into the liquid.

Since a key feature incorporated into the present invention includes the portability of the entire apparatus 10, the exemplary distribution and supply manifold 40 includes an interface for inputting power (interface 42) and water (interface 44) from an on-site industrial or municipal source. With such intended utility inputs, it is envisioned that the inclusion of power or water conditioning mechanisms, such as, for example, a power line conditioner or water filtration through sieving, adsorption, screening or ion exchanges, can be incorporated in a self-contained and portable manner such as to provide the capability of stabilizing and controlling the inputs to the overall apparatus 10.

In the illustrated embodiment, the controller 30 is in operative communication with and control of the supply manifold 40, and may store sensor and instrument inputs such as flow rates, fill volumes, oxygen concentration, pH, and temperature. The bioreactor 20 may include a heating plate, heating jacket, or other mechanism to raise the temperature, as well as inlet ports for adding acid or caustic solutions for control of pH, as well as nutrients, water or air in order to reach and maintain optimum conditions for the desired biosynthesis to occur.

The supply manifold 40 is in fluid and thermal communication with the bioreactor 20, and is operatively controlled by the controller 30. The achieving or maintaining of suitable fermentation conditions may be maintained and acted upon by the controller, and as such a provision for addition of fluids is provided by peristaltic type metering addition pumps 32 or other pumps 34. Materials to be added or controlled may include pH control agents (such as acid or caustic solutions), defoaming agents, oxygen or air, water and other liquid media.

Figure 6:
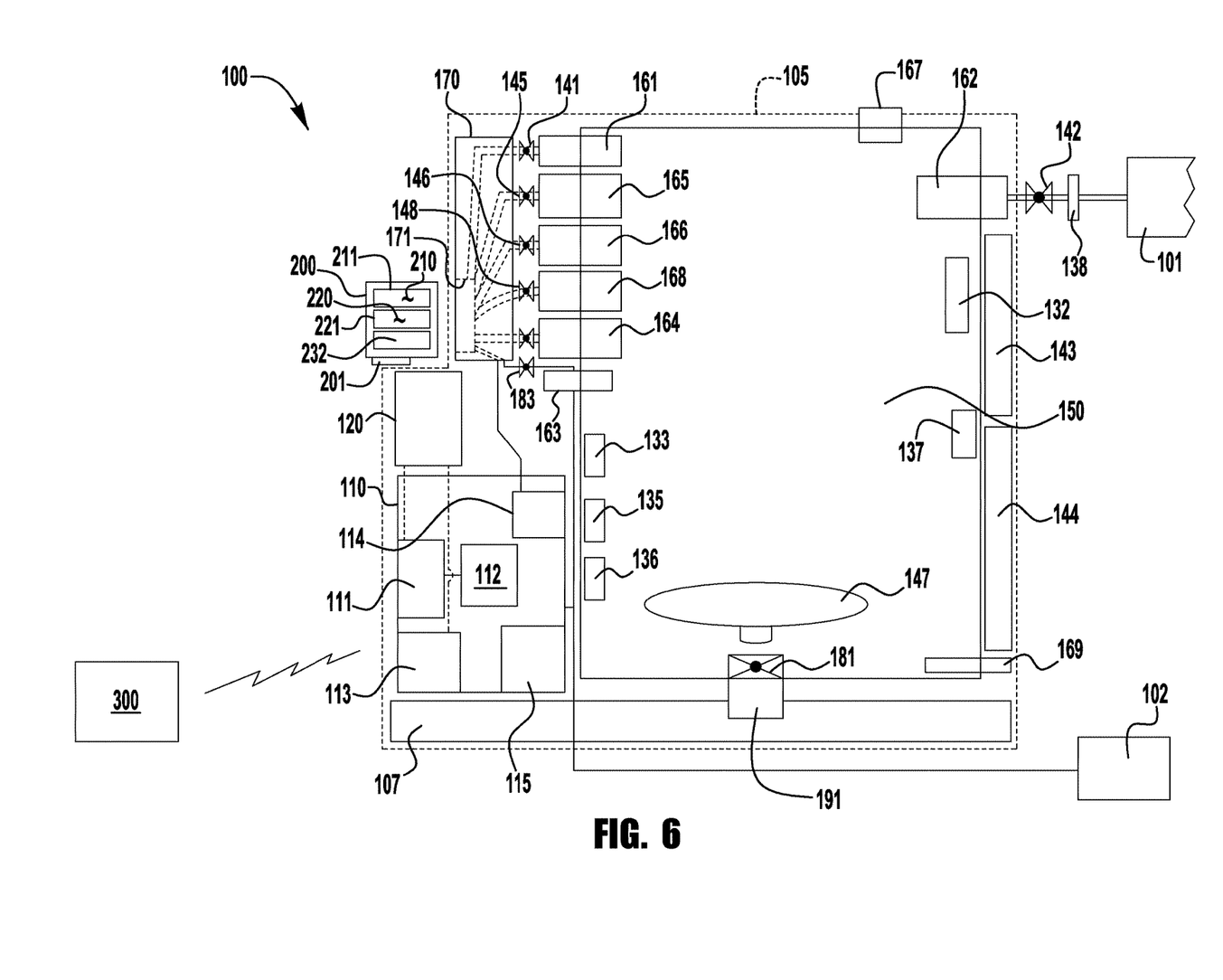
FIG. 6 is a schematic illustration of an exemplary fermentation system.

According to an inventive aspect of the present application, as schematically shown in FIG. 6, a fermentation system 100 may be provided with a bioreactor 105 carried by a platform or frame 107, which may be a mobile (e.g., wheeled and provided with a trailer hitch) frame to provide for portable, on-site fermentation, as described above. The bioreactor 105 includes a fermentation tank 150 for containing microbiological culture and growth media in a controlled environment, and a controller 110 (e.g., a program logic controller, or PLC) configured to control one or more automated system settings or adjustments of the fermentation process, and to direct user implementation of one or more steps of the fermentation process requiring manual user activity (e.g., addition of starter culture or growth media). As used herein, the term "controller" may include multiple controlling devices (e.g., multiple PLC's), disposed in one or more locations on the bioreactor. The controller may be electrically connected with, and powered by, an external power source 102, or by one or more battery cells (not shown) carried by the bioreactor.

The system may be provided with a user interface 120 for receiving information from the user about the bacteria (or other microorganism) to be cultured. The user interface 120 (e.g., a touch-screen monitor) may be assembled with the bioreactor 105, and in wired communication with a receiver circuit 111 of the controller 110. In other embodiments, the user interface may be a portable computing device (e.g., a smart phone, tablet, or laptop computer) provided with software or a web-based application configured to communicate wirelessly with the receiver circuit of the controller (e.g., using RFID, Bluetooth, NFC, WiFi, cloud computing, or cellular communication).

The exemplary controller 110 is programmed to store, in a memory 112, a recipe for one or more selectable fermentation batches (e.g., bacteria), with the recipe identifying suitable conditions for growing a selected microorganism, including, for example, water volume, temperature, oxygen content, pH, turbidity, and amount and/or type of nutrients. This recipe may be specific to the bioreactor used, as properties of the bioreactor (e.g., tank volume, tank shape, aspect ratio, cooling & heating capacity, and oxygen availability) may affect the fermentation process.

To initiate preparation of a batch using the fermentation system 100, the user identifies to the controller 110 (e.g., through user interface 120 communication to the receiver circuit 111) the particular batch to be prepared in the bioreactor 105, such that the controller may associate the identified batch with a corresponding stored recipe. While the user may identify the batch by selecting a bacterium or other microorganism from a list displayed on the user interface, in other embodiments, the batch may be identified using a batch identification code provided to the user, for example, to prevent the user from misidentifying the batch by selecting an incorrect bacterium (e.g., a bacterium with a similar sounding name). This identification code may be provided to the user by a controlling entity (e.g., the manufacturer/provider of the bioreactor 105, or the supplier of the fermentation kit 200), for example, by telephone, text message, or web-based communication. In other embodiments, the identification code may be provided with the materials provided to the user (e.g., the starter culture and the nutrient media), and may be read off of one or more of the containers or packaging elements 201 of these materials and manually entered using the user interface 120. In still other embodiments, the identification code may be received by the controller, either directly or through the user interface, without manual input of the code by the user, thereby avoiding accidental mis-entry by the user. Examples include bar code identifiers on the packaging element 201 that may be scanned by the user interface 120 and communicated to the controller 110, RFID tags (embedded in or carried by the packaging element 201) that may be read by an RFID transceiver in the controller or in the user interface (for communication to the controller), or a memory storage device (e.g., a PC board, flash drive, or memory card, embedded in or carried by the packaging element 201 or some other kit component) that is electrically connectable with the user interface 120 or controller 110 for wired communication with the user interface or controller.

Materials specific to the batch to be prepared by the user, such as, for example, a starter culture 210 and a nutrient media 220, may be provided to the user in a kit 200 (e.g., in containers or reservoirs 211, 221) in predetermined amounts and controlled quality to facilitate successful preparation of the desired batch.

When a desired batch is successfully identified to the controller 110, the controller accesses the corresponding stored recipe in memory 112 to initiate the fermentation process. In an exemplary embodiment, the recipe for the selected batch includes stored information corresponding to the steps and required parameters of the fermentation process. This fermentation process may include some automated steps and settings that may be performed and controlled by electronically controlled mechanisms of the bioreactor (e.g., valves, motors, heating elements, pumps, etc., as described below) as directed by a control circuit 114 of the controller 110, and monitored by sensors (e.g., temperature, water level, turbidity, pH, dissolved oxygen, and other sensors, as described below) provided with the fermentation tank 150 and in communication with a sensor circuit 115 of the controller 110. Automatic addition of materials to the fermentation tank, as directed by the controller, may be managed at a supply manifold 170 housing and/or supporting valves, pumps, injectors, and/or conduits for selectively supplying the materials to the tank as directed by the controlling circuit 114 of the controller 110. The fermentation process may also include some manual steps requiring physical actions by the user (e.g., supplying the starter culture and nutrient media to the bioreactor). These manual steps may be performed by the user at the direction of the controller, through prompts communicated from a transmitting circuit 113 of the controller to the user through the user interface 120.

In an exemplary recipe-controlled fermentation process, the controller 110, through the control circuit 114, first initiates a pre-programmed clean in place (CIP) process (e.g., stored in the memory 112 as part of the material specific recipe), for example, passing a cleaning fluid (e.g., peracetic acid/PPA, surfactants, enzymes) through an internal nozzle 161 (e.g., spray ball type nozzle) into the fermentation tank 150, through controller circuit operation of a CIP valve 141. The recipe-based preset program may control the time (e.g., 45-90 minutes) and temperature (e.g., 80° C.-90° C.) of the CIP process, followed by a preset draining and rinsing operation for a preset time period (e.g., 30-60 minutes).

The fermentation tank 150 of the bioreactor is then filled with a preset volume of water (e.g., 80-95 liters) by automatic controller (control circuit) operation of a water supply valve 142, with the water passing through a suitable filtration system 138 (e.g., a 0.1 to 0.5 micron, three stage system) to a water inlet port 162. The controller may monitor the condition of the filter (e.g., by monitoring flow rate from a flow sensor or by clock-based service life) to insure proper water quality. The water supply valve 142 may be connected with an external water source 101 or to a self-contained water source of the fermentation system (not shown). The water is heated to a desired preset sterilization temperature (e.g., 70° C.-90° C.) by automatic control circuit operation of a heating element 143 (e.g., heating plate, heating coil, or water heated jacket). Once the sterilization temperature is reached, as determined by a temperature sensor 133 in communication with the controller 110, the controller (transmitting circuit) prompts the user (through communication from the transmitting circuit 113 to the user interface 120) to add a predetermined amount (e.g., 1-40 kg) of a media mixture 220 (e.g., a liquid media, such as molasses, or a solid media, such as corn peptone or NPK fertilizer) to the water in the fermentation tank, for example, through an addition port 163, or in the case of larger volumes of nutrients, through a pump system. The media mixture may be provided to the user in the desired amount in a pre-packaged kit, as described in detail below, and the controller may be configured to receive a separate identification code associated with the packaged media mixture (e.g., by manual user entry of a code on a packaging label, bar code scanning of a packaging label, or RFID communication with an embedded RFID tag) to confirm that the proper amount and type of nutrient media is being used. After re-heating the water and media to the sterilization temperature (using the heating element 143 and temperature sensor 133 in communication with the controller 110), the media is held at this temperature for a preset period of time (e.g., 30-90 minutes, depending on media characteristics) to sterilize the media.

After media sterilization is completed, the controller 110 initiates a cooling cycle (e.g., through operation of a cooling jacket 144) to cool the media to a preset fermentation temperature (e.g., 20° C.-65° C., depending on the type of culture being prepared) in preparation for starter culture inoculation. Once the fermentation temperature is stabilized, as determined by the temperature sensor, the controller 110 prompts the user (through communication from the transmitting circuit 113 to the user interface 120) to add the starter culture to the fermentation tank (through the media addition port 163, or through a different addition port). Before prompting the user to add the starter culture, the controller 110 may prompt the user (through communication from the transmitting circuit 113 to the user interface 120) to sterilize the addition port, for example, through heating of the addition port (e.g., using a propane torch supplied with the fermentation kit). As with the media mixture, the starter culture may be provided to the user in the desired amount in a pre-packaged kit, as described in detail below, and the controller 110 may be configured to receive a separate identification code associated with the packaged starter culture (e.g., by manual user entry of a code on a packaging label, bar code scanning of a packaging label, or RFID communication with an embedded RFID tag) to confirm that the proper amount and type of starter culture is being used.

Once the starter culture has been added, the controller initiates (through the controlling circuit) an automated fermentation cycle, which may range from 2-48 hours depending on the type of culture being fermented and the volume of the batch being prepared. During this cycle, the controller, through the sensing and controlling circuits, monitors and adjusts parameters required for successful fermentation, and specific to the stored batch recipe, including, for example: temperature (as sensed by the temperature sensor 133, through operation of the heating and cooling elements 143, 144), water level (as sensed by a water level sensor 132, through operation of the water supply valve 142), pH (as sensed by a pH sensor 135, through operation of a pump and/or acid/base agent supply valve 145 to supply acid/base agent through a supply port 165), turbidity (as sensed by an optical density sensor 136, through operation of a pump and/or defoaming agent supply valve 146 to supply a defoaming agent through a supply port 166), oxygen content (as sensed by a dissolved oxygen sensor 137, through operation of one or more impellers, air spargers, air flow or air lift mechanisms 147, a pump/valve 148 supplying oxygen generating or oxygen dissolving chemicals through a supply port 168, or operation of a ventilation port). The controller 110 records and maintains graphical and digital records of the levels of these parameters over time, and the adjustments made by the system.

At preset intervals during the fermentation cycle, the controller 110 prompts the user (through communication from the transmitting circuit 113 to the user interface 120) to take samples from the fermentation tank (for example, using a sample port 169) to validate the cell growth using a bacterial growth monitor (e.g., a hand held optical density (OD) scanner, manufactured, for example, by BugLab LLC). The cell growth data may be recorded and stored off line and communicated to the controller. The controller 110 may be programmed to wirelessly transmit (e.g., through transmitting circuit 113) at recipe-based preset intervals (e.g., 30 seconds to 10 minutes, depending on the type of culture and fermentation time) the graphical/digital system data and any recorded cell growth data to a remote system 300 (e.g., central computer system or cloud-accessing computer) for remote monitoring of the fermenter operations.

The parameters monitored by the controller 110 are compared to recipe-based critical limits. If a parameter falls within a predetermined range of a critical limit, the controller alerts the user through the user interface 120 (e.g., a warning light, alarm sound, warning screen message, text or phone message to a user's smart phone). The controller may be configured to maintain this alert until the operator manually confirms (e.g., by pressing a button or touch-screen prompt on the user interface 120) that the bioreactor system has been checked for obvious equipment issues (e.g., leaks, damage) The same alert may be wirelessly communicated to the remote computer system 300. If a parameter exceeds a critical limit, the controller 110 may be configured to automatically shut down the fermentation cycle and suspend batch operations, and may, for example, lock discharge valves against release of the bacteria slurry, or open the fermentation tank to drainage for disposal of the bacteria slurry. The fermentation system may remain in a shutdown condition until being cleared by a controlling entity, for example, through remote wireless communication between the remote computer system 300 and the controller 110.

Once the batch cycle is complete, as determined by recipe-based elapsed time, dissolved oxygen (DO), or biomass parameters, the controller initiates a batch stabilization mode, controlling the tank temperature, pH, and mixing in accordance with recipe based parameters (through operation of the parameter controlling mechanisms and monitoring of the sensors, as described above), for preservation of the bacteria. The controller, through the user interface, or by text or phone message to the user's cell phone, notifies the user that the batch cycle is complete. The controller, through the user interface, instructs the user as to the proper fluid system configuration (e.g., valve settings and line connections) required for harvest of the bacteria slurry. Once establishment of this configuration has been confirmed by the user, the controller unlocks the drain valve 181 for release and harvest of the bacteria slurry through a drain port 191.

The controller may then prompt the user to take final batch samples for analysis, and release of the batch for collection may be conditioned by the controller on the results of this analysis. A final batch record of parameters and conditions of the batch and the batch fermentation process may be transmitted, along with the batch sample analysis results, to a remote computer system, and the batch samples may be shipped to a central office or repository for storage. The completed batch is collected in one or more containers by the user. The controller or the remote computer system may generate a batch code to be associated with the batch record and the stored samples, by which the collected batch may be identified (e.g., by labeling the containers with the batch code). This single use batch code can ensure that the batch may be tracked back to the fermentation system and parameters used to generate it.

According to another inventive aspect of the present application, a fermentation kit for a fermentation system may be adapted to utilize a self-contained cartridge of materials usable to effectively grow a batch of bacteria slurry or other microbiological product. The cartridge may include, for example, a starter culture material and optionally, one or more of a sterilization material (e.g., for cleaning the bioreactor before and/or after the fermentation process), a nutrient material (for fueling the bacterial growth), acidic and/or caustic solutions (for adjustment of the pH of the fluid), and a defoaming agent (for reducing excessive foaming). By providing these materials with the cartridge, it may be ensured that sufficient materials are available for a successful batch generation of the desired microbiological product, as may be required by the stored recipe corresponding to that microbiological product. The cartridged material arrangement may also provide for increased control of the quality and type of materials used during the fermentation process. The cartridge prevents genetic drift, providing a fresh starter culture insuring exactly the same batch every time. The cartridge may prevent the operator from using the wrong fermentation materials or amounts, since the programs may be coded into the controller. The cartridge prevents unauthorized microbes for being fermented, since the unit will not operate without the proper validation code provided with or for that fermentation cartridge.

While this cartridge may function as little more than a kit from which the user may obtain and dispense the provided materials as needed, in other embodiments, as shown in FIG. 6, the cartridge 200 is connectable or installable with a process control system of the bioreactor (e.g., received in a port 171 of the supply manifold 170) to provide fluid connections between storage chambers 211, 221, 232) in the cartridge 200 for each of the materials contained within the cartridge, and corresponding supply ports to the bioreactor, with controller operated valves, pumps, and/or injectors providing selective supply of these material through the corresponding ports as needed. For example, a starter culture chamber 211 of the installed cartridge 200 is connected with a culture supply port 163 of the bioreactor by an injector 183. Where a sanitization material is provided with the cartridge, a sanitization material chamber (not shown) of the installed cartridge may be connected with the CIP supply port 161 by CIP valve 141 for cleaning of the fermentation tank. As another example, an acid/caustic solution chamber 232 of the installed cartridge 200 may be connected with a pH adjustment supply port 165 by acid/base agent supply valve 145. As still another example, a defoam chamber (not shown) of the installed cartridge may be connected with a defoam supply port 166 of the bioreactor through the defoam supply valve 146. The materials provided with the cartridge may be automatically supplied to the fermentation tank as directed by the controller (through control circuit operation of the corresponding fluid control valve/pump/injector), for example, in response to information provided to the controller by one or more of the system sensors described above.

In one embodiment, a user may input information (e.g., through a user interface) regarding the culture being developed in conjunction with connection of a cartridge to the process control system. For example, the cartridge may be provided with a printed serial number or product number that is stored in the controller memory and associated with a stored recipe or program corresponding to the starter culture stored in the cartridge. According to another aspect of the present application, a process control system and batch initiation cartridge may be configured for direct communication of the stored starter culture and any other useful information (e.g., temperature, oxygen levels, pH, cycle time, shock cycle) regarding the fermentation process to be performed. This arrangement may eliminate user error in entry of information corresponding to the fermentation process to be performed.

Many different systems or arrangements may be utilized to provide this communication. As one example, the cartridge may be provided with a bar code or alphanumeric code that can be scanned by the process control system, either before or after connection of the cartridge with the process control system. As another example, the cartridge may be provided with an RFID tag that may be read by an RFID reader associated with the process control system when the cartridge is connected to or placed in proximity with the process control system. As still another example, the cartridge may include a memory electrically connectable with and accessible by the process control system when the cartridge is physically connected with the process control system. In some such embodiments, the program or recipe for processing the stored culture may be stored in the memory of the cartridge and written to the process control system upon connection of the cartridge.

In some embodiments, such cartridges may be retained for reuse, refurbishing, refilling or recycling. Cartridges may be manufactured or otherwise prepared at a central control location and subsequently provided to one or more remote operational locations having proper starter culture and other process support materials, filters, and customized with system programming information as described above. The spent cartridge may be returned to the central control location to be reprocessed or recycled for a subsequent run. Each cartridge may be coded for identification, reconciliation, and otherwise for maintaining or providing information related to product tracing under various supply chain management regimes or regulatory regimes including, inter alia, the Food Safety Modernization Act or the like. Since the major causes for improper batch production include improperly filtered water, lack of proper chemicals, programming error, improper air filtration, improper charging of starter culture, these major sources of reduced yield are prevented. Further, the use of initiation cartridges helps to prevent improper use of the batch and is a security system to prevent use of unapproved starter cultures. In some embodiments, at least one of the process control system and the cartridge stores information regarding the use of the cartridge, for example, to prevent its reuse without appropriate reconditioning of the cartridge, effectively limiting the cartridge to a single authorized use.

Various element and functions may be incorporated within an initiation cartridge 58 and in various combinations or permutations. For purposes of disclosure and not meant as a limitation, a cartridge may incorporate the following cartridge components:

Lyoyophilized bag of starting bacteria with integral connection system to the system controller;
Three stage filter to remove bacteria from potable water;
Air filter;
Buffer chemicals for pH adjustment utilizing a refillable tank with fluid communication connection;
Buffer chemicals to defoam utilizing a refillable tank with a fluid communication connection;
Cleaning support chemicals utilizing a refillable tank with a fluid communication connection;
RFID tag to integrate cartridge to program the controller;
Water system provided filtered, temperature controlled water to the reactor;
Connection for clean-in-place (CIP) and sterilization-in-place (SIP) system;
A potable water connection;
An electrical power system connection; and
Validation sensors In an exemplary embodiment, a cartridge contains starter culture, saline solution, defoamer, acid, base, and injection tools. These are all sterile and shipped in sealed unit. Operator scans RFID tag to activate program. The operator follow prompts through CIP and sterilization. The acid, base, and defoamer are placed in coded receptacles which attached to patristic pumps. The operator is then prompted to mix mediate with saline and inoculate solution through injection port with sterile syringe provided in kit. The unit commence with fermentation process using preprogrammed setting. The status of the batch is show on screen for operator and transmitted to laboratory for review by cellular communication. The batch corrections for temperature, air flow, air lift operation, foam removal, and pH adjustments are made by the program. Once cycle is complete, operator is prompted through discharge procedures.

Figure 3:
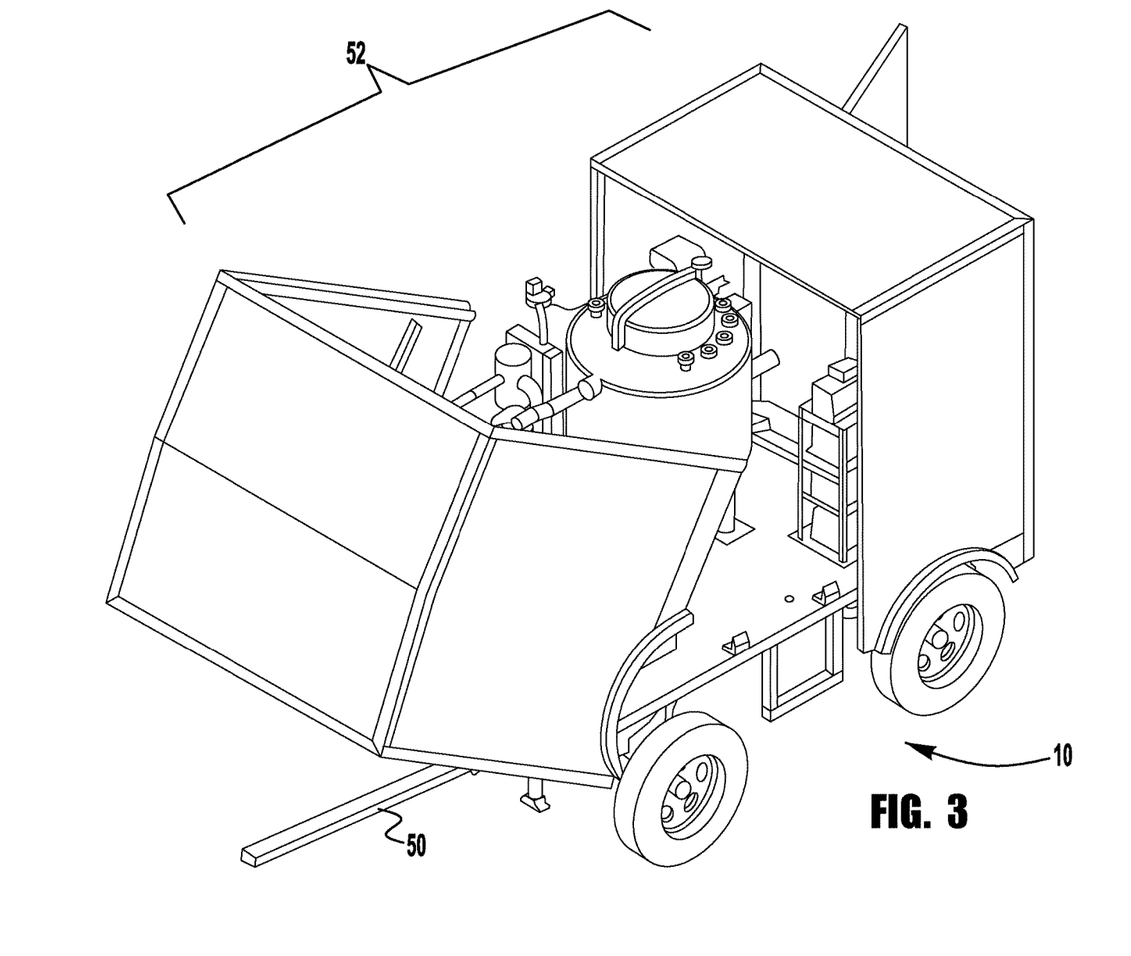
FIG. 3 is a front top perspective view thereof shown in conjunction with a portable trailer in a partially opened configuration.
Figure 4:
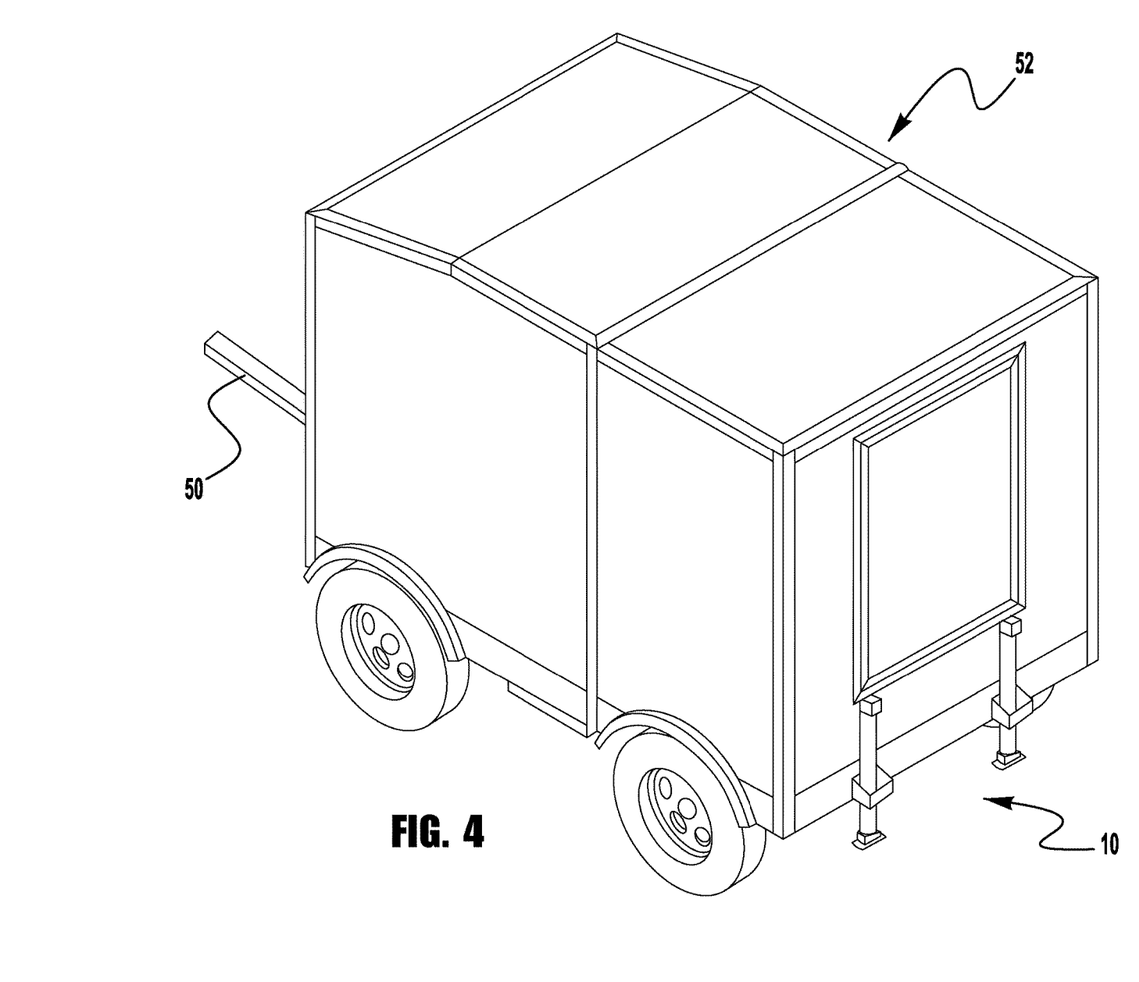
FIG. 4 is a rear top perspective view thereof shown in conjunction with a portable trailer in a closed configuration.
Figure 5:
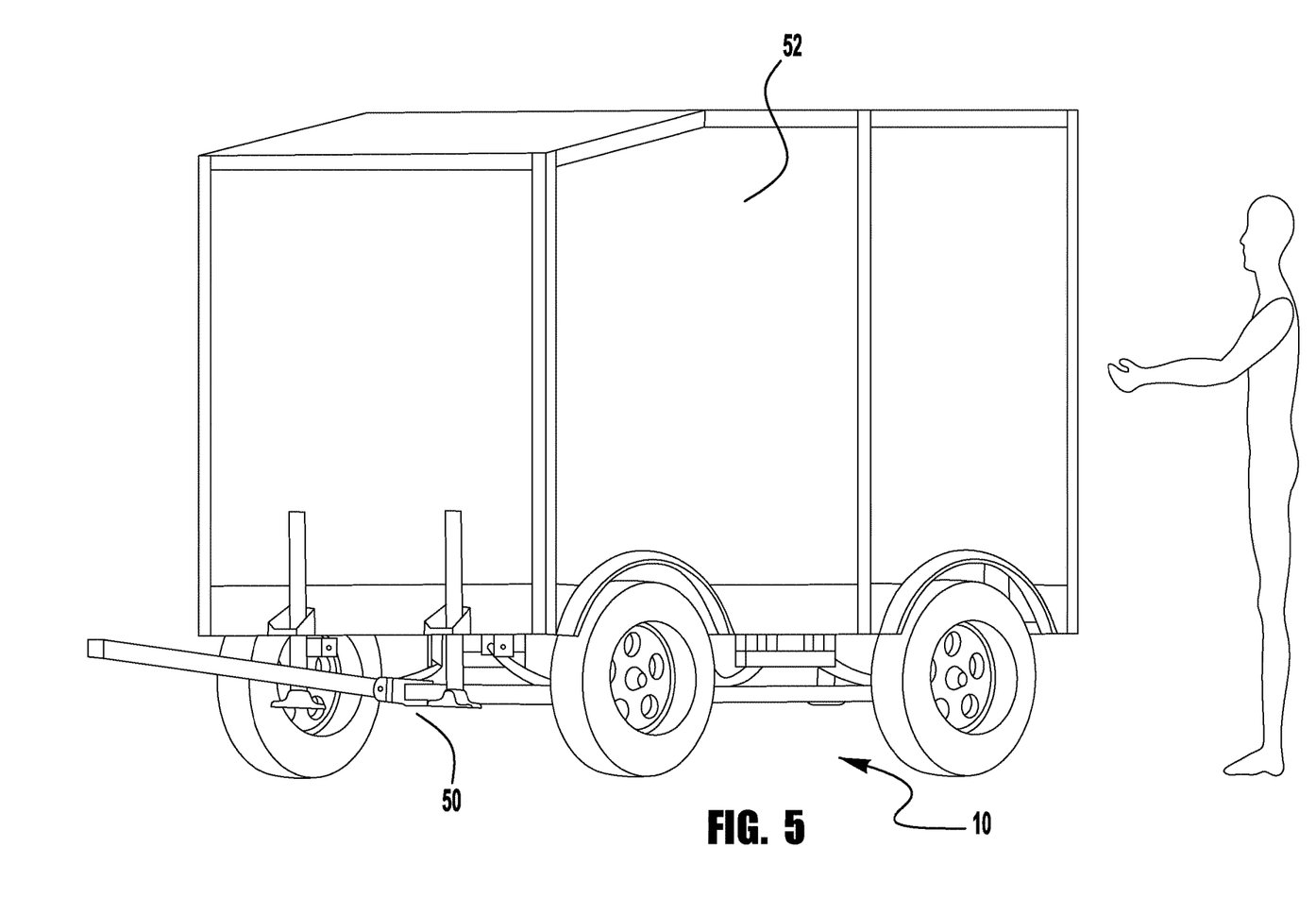
FIG. 5 a front side perspective view thereof.

Referring now in conjunction with FIG. 3 through FIG. 5, the apparatus for culturing and delivering microorganism products 10 includes a portable frame or support structure 50 having a portable trailer 52 having configurable enclosures. Such a configuration allows for the easy, portable deployment of a plurality of devices for culturing and delivering microorganism products 10 throughout various environments for subsequent delivery at a radius from the production source at less than approximately 48 hours of total time to delivery and use, or less than approximately 400 miles. Such portability enables a method for culturing and delivery biologically active products is provided utilizing the deployment of a portable bioreactor mechanism within an effective distribution radius, and subsequently delivering the biologically active product to a target environment within said effective distribution radius.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A method of preparing a batch of microbiological material, the method comprising:
   providing a fermentation kit to a user, the fermentation kit comprising a starter culture;
   providing a fermentation system comprising a fermentation tank, a plurality of sensors operable to measure a plurality of fermentation system parameters, a plurality of mechanisms operable to control the plurality of fermentation system parameters, and a controller in electronic communication with the plurality of sensors and with the plurality of mechanisms, wherein the controller includes a memory having stored therein a plurality of recipes each defining user operating instructions and parameter settings specific to fermentation of one of a plurality of microbiological cultures including the starter culture;
   providing a batch identification code to a user, the batch identification code being associated in the memory of the controller with the one of the plurality of recipes specific to the starter culture;
   communicating the batch identification code to the controller;
   communicating, from the controller to the user, the operating instructions defined by the associated one of the plurality of recipes, the operating instructions including instructions for one or more manual user operations performed using the fermentation system; and
   using the controller, operating the plurality of mechanisms to adjust the plurality of fermentation system parameters in accordance with the parameter settings defined by the associated one of the plurality of recipes.

2. The method of claim 1, wherein the one or more manual user operations include at least one of adding the starter culture to the fermentation tank, adding a nutrient material to the fermentation tank, adding a pH adjusting agent to the fermentation tank, adjusting air flow, and adjusting dissolved oxygen levels.

3. The method of claim 1, wherein providing the batch identification code to the user comprises displaying the batch identification code on a packaging element provided with the fermentation kit.

4. The method of claim 1, wherein providing the batch identification code to the user comprises communicating the batch identification code to the user via at least one of electronic mail, text message, telephone message, software-based application, and web-based application.

5. The method of claim 1, wherein communicating the batch identification code to the controller comprises receiving at the controller user entry of the batch identification code through a user interface in communication with the controller.

6. The method of claim 5, wherein the user interface comprises a touch screen assembled with the fermentation system in circuit communication with the controller.

7. The method of claim 5, wherein the user interface comprises a portable computing device in wireless communication with the controller.

8. The method of claim 1, wherein providing the batch identification code to the user comprises providing in the fermentation kit a memory storage device storing the batch identification code.

9. The method of claim 8, wherein the memory storage device is configured to communicate wirelessly with the controller to transmit the batch identification code to the controller.

10. The method of claim 8, wherein the memory storage device is configured to be electrically connected with the controller to transmit the batch identification code to the controller.

11. The method of claim 1, wherein communicating the batch identification code to the controller comprises optical scanning of a bar code displayed on a packaging element of the fermentation kit.

12. The method of claim 1, further comprising disassociating the batch identification code from the associated one of the plurality of recipes after communicating the batch identification code to the controller, thereby preventing reuse of the fermentation system using the batch identification code.

13. The method of claim 1, wherein operating the plurality of mechanisms to adjust the plurality of fermentation system parameters includes at least one of adding a nutrient material to the fermentation tank, adding water to the fermentation tank, adding air to the fermentation tank, adding a pH adjusting agent to the fermentation tank, adding a defoaming agent to the fermentation tank, operating a heating element, operating a cooling element, operating an air sparger, operating a ventilation port, operating a drain valve, and adjusting mixing.

14. The method of claim 1, wherein the fermentation kit comprises a cartridge, wherein communicating the batch identification code to the controller comprises electrically connecting the cartridge with the fermentation system.

15. The method of claim 1, wherein the fermentation kit comprises a cartridge connectable to the fermentation system, wherein operating the plurality of mechanisms to adjust the plurality of fermentation system parameters includes extracting from the cartridge and adding to the fermentation tank at least one of the starter culture, a nutrient material, a pH adjusting agent, a defoaming agent, a sterilizing fluid, and dissolved oxygen enhancing agents.

* * * * *